(12) United States Patent
Okamura et al.

(10) Patent No.: US 7,749,760 B2
(45) Date of Patent: Jul. 6, 2010

(54) Vγ9Vδ2 T CELL PROLIFERATION AGENT, METHOD FOR PRODUCING ACTIVATED Vγ9Vδ2 T CELLS, AND USES THEREOF (75) Inventors: Haruki Okamura, Ibaraki (JP); Shuji Kubo, Ashiya (JP); Wen Li, Nishinomiya (JP)

(73) Assignee: Hyogo College of Medicine, Hyogo-ken (JP)

( * ) Notice: Subject to any disclaimer, the term of this patent is extended or adjusted under 35 U.S.C. 154(b) by 0 days.

(21) Appl. No.: 12/316,973

(22) Filed: Dec. 17, 2008

(65) Prior Publication Data

US 2010/0009447 A1    Jan. 14, 2010

(30) Foreign Application Priority Data

Jul. 10, 2008   (JP)   ............................. 2008-180749

(51) Int. Cl.
   *C12N 5/078*   (2010.01)
   *C12N 5/0783*  (2010.01)
   *C07K 14/54*   (2006.01)
   *C07F 9/40*    (2006.01)

(52) U.S. Cl. ...................... 435/377; 435/325; 530/351; 548/112

(58) Field of Classification Search .................. None
See application file for complete search history.

(56) References Cited

U.S. PATENT DOCUMENTS

| | | | |
|---|---|---|---|
| 6,534,050 B1 | 3/2003 | Tanaka et al. | |
| 2003/0152551 A1 | 8/2003 | Tanaka et al. | |

FOREIGN PATENT DOCUMENTS

| | | |
|---|---|---|
| JP | 4025019 B2 | 12/2007 |
| WO | WO-2006/006720 A1 | 1/2006 |

OTHER PUBLICATIONS

Eberl et al, Cellular Immunology, 2002, vol. 218, pp. 1-6.*
Garcia et al, The Journal of Immunology, 1998, vol. 160, pp. 4322-4329.*
Price et al, Immunology, 2006, vol. 120, pp. 57-65.*
Japanese Office Action from corresponding Japanese Application No. 2008-180749 and English translation.
Volker Kunzmann et al., "Stimulation of γδ T cells by aminobisphosphonates and induction of antiplasma cell activity in multiple myeloma" Blood, Jul. 15, 2000, vol. 96, No. 2, p. 384-392.
Dieter Kabelitz et al., "Characterization of Tumor Reactivity of Human V γ 9V δ 2 γδ T Cells in Vitro and in SCID Mice in Vivo" The Journal of Immunology, 2004, vol. 173, p. 6767-6776.
V. Ferlazzo et al., "In Vitro Effects of Aminobisphosphonates on V γ 9Vδ2 T Cell Activation and Differentiation" International Journal of Immunopathology and Pharmacology, 2006, vol. 19, p. 309-317.
Tadashi Saito et al., "Orally administrated risedronate can commit Vγ2Vδ2 T cells to IFN-γ secreting effectors in patients with osteoporosis" Biomedical Research, 2004, vol. 25, p. 1-8.
Karen Schilbach et al., "Induction of proliferation and augmented cytotoxicity of γδ T lymphocytes by bisphosphonate clodronate," Blood, May 1, 2001, p. 2917-2918, vol. 97 No. 9.
Nadia Caccamo et al., "Aminobisphosphonates as New Weapons for γδ T Cell-Based Immunotherapy of Cancer," Current Medical Chemistry, 2008, p. 1147-1153, 15.
Kiyoshi Sato et al., "Cytotoxic effects of γδ T cells expanded ex vivo by a third generation bisphosphonate for cancer immunotherapy," Int. J. cancer, 2005, p. 94-99, 116.
Haruki Okamura et al., "Cloning of a new cytokine that induces IFN-γ production by T cells," Nature, Nov. 2, 1995, p. 88-91, vol. 378.
Wen Li et al., "Protection of CD8+ T cells from activiation-induced cell death by IL-18," Journal of Leukocyte Biology, Jul. 2007, p. 142-151, vol. 82.

* cited by examiner

*Primary Examiner*—Gary B. Nickol
*Assistant Examiner*—Fozia M Hamud
(74) *Attorney, Agent, or Firm*—Edwards Angell Palmer & Dodge LLP; David G. Conlin; Lisa Swiszcz Hazzard (57) ABSTRACT

A Vγ9Vδ2 T cell proliferation agent includes at least a bisphosphonate, interleukin 2, and interleukin 18. Since IL-18 has properties that improve cell viability by inhibiting cell death, IL-18 is presumably capable of acting as a cofactor for the bisphosphonate so as to significantly increase the effect of Vγ9Vδ2 T cell proliferation by the bisphosphonate and the IL-2. This allows providing a Vγ9Vδ2 T cell proliferation agent capable of growing Vγ9Vδ2 T cells with a proliferated efficiency significantly high compared to conventional methods so that the proliferated Vγ9Vδ2 T cells have a high antitumor activity and high cytokine productivity.

3 Claims, 6 Drawing Sheets

Vγ9Vδ2 T CELL PROLIFERATION AGENT, METHOD FOR PRODUCING ACTIVATED Vγ9Vδ2 T CELLS, AND USES THEREOF

This Nonprovisional application claims priority under 35 U.S.C. §119(a) on Patent Application No. 180749/2008 filed in Japan on Jul. 10, 2008, the entire contents of which are hereby incorporated by reference.

FIELD OF THE INVENTION

The present invention relates to a Vγ9Vδ2 T cell proliferation agent, a method for producing activated Vγ9Vδ2 T cells, and use of the proliferation agent and the activated Vγ9Vδ2 T cells. More particularly, the present invention relates to (i) a Vγ9Vδ2 T cell proliferation agent containing at least a bisphosphonate, interleukin 2, and interleukin 18, (ii) a method for producing activated Vγ9Vδ2 T cells, the method comprising stimulating Vγ9Vδ2 T cells by using at least a bisphosphonate, interleukin 2, and interleukin 18, (iii) the activated Vγ9Vδ2 T cells and a medicine containing the same, and (iv) a Vγ9Vδ2 T cell proliferation kit.

The Vγ9Vδ2 T cell proliferation agent of the present invention contains at least bisphosphonate, interleukin 2, and interleukin 18. This allows dramatic proliferation of Vγ9Vδ2 T cells, whose efficient proliferation method has not been developed conventionally. Therefore, the present invention is suitably applicable to various industries relating to biochemistry, such as pharmaceutical industry.

BACKGROUND OF THE INVENTION

Vγ9Vδ2 T cells (Vγ9Vδ2 T lymphocyte) are spotlighted as cells capable of performing tumor cell elimination and intracellular defense against parasitic bacteria and parasites without being restricted by major histocompatibility antigens. Cancer treatment with use of Vγ9Vδ2 T cells obtained from human peripheral blood is currently under research. However, a limited quantity of Vγ9Vδ2 T cells present in human peripheral blood makes it difficult to obtain a sufficient amount of Vγ9Vδ2 T cells for use in immunotherapy.

A recent report demonstrated that bisphosphonates, which are used, for example, for osteoporosis treatment, exhibit antitumor action by acting directly on cancer cells, and also act on γδ T cells to encourage growth and activation of γδ T cells (Blood, 97:2917-2918, 2001). γδ T cells thus proliferated have a strong antitumor cell activity. Many studies have been conducted to establish therapies in which γδ T cells separated from blood of a cancer patient's own are proliferated in vitro using a bisphosphonate, and the lymphocytes thus obtained are returned to the body. Some studies reported promising results (Curr. Med. Chem., 15:1147-1153, 2008). In addition, there is disclosed a method (see Japanese Patent No. 4025019; registered on Oct. 12, 2007) in which the proliferation of Vγ2Vδ2 T cells is carried out with addition of an organic pyrophosphate derivative and use of interleukin 2 (hereinafter abbreviated as "IL-2") as a cofactor. There is also disclosed another method (see Int. J. Cancer 116, 94-99, 2005) in which the proliferation of Vγ9Vδ2 T cells is carried out with addition of zoledronate and use of IL-2 as a cofactor.

However, such conventional arts have a problem in that Vγ9Vδ2 T cells cannot be proliferated sufficiently. For example, with the addition of zoledronate and IL-2, proliferation gain of Vγ9Vδ2 T cell can be improved only up to about 800 fold maximally (Int. J. Cancer 116, 94-99, 2005). With such a low proliferation gain, this method requires a large number of Vγ9Vδ2 T cells to be proliferated. This necessitates collecting a large amount of peripheral blood from the patient, thereby giving the patient much pain and burden.

Under such circumstances, an art is long awaited that enables more efficient proliferation of Vγ9Vδ2 T cells for establishment of a cancer treatment using Vγ9Vδ2 T cells.

SUMMARY OF THE INVENTION

The present invention has been accomplished in view of the above problem. It is an object of the present invention to provide (i) a Vγ9Vδ2 T cell proliferation agent capable of growing Vγ9Vδ2 T cells with a significantly high growth efficiency compared to conventional arts so that the proliferated Vγ9Vδ2 T cells have a high antitumor activity and high cytokine productivity, (ii) a method for producing activated Vγ9Vδ2 T cells, and (iii) the usage of the proliferative agent, the method, and the activated Vγ9Vδ2 T cells.

The inventors diligently studied the above problem and confirmed that, compared to conventional methods, a significant increase of the Vγ9Vδ2 T cells can be attained when lymphocytes separated from peripheral blood are cultured in a medium supplemented with IL-2, a bisphosphonate, and interleukin 18 (hereinafter referred to as "IL-18"). Furthermore, the inventors found that such Vγ9Vδ2 T cells thus obtained have a high antitumor activity and high ability to produce cytokines such as interferon-gamma (hereinafter abbreviated as "IFN-γ"). The present invention was accomplished based on these findings.

In order to attain the above object, a Vγ9Vδ2 T cell proliferation agent of the present invention includes at least a bisphosphonate, interleukin 2, and interleukin 18.

IL-18 is a cytokine discovered by Okamura et al. in 1995 as an IFN-γ inducing factor (Okamura et al., Nature 378:88-91, 1995). It has been revealed in recent years that IL-18 has various biological actions. The inventors of the present invention have reported that IL-18 significantly increases the population sizes of activated CD8-positive T lymphocytes and NK cells by inhibiting apoptosis of such cells, and that the activated CD8-positive T cells strongly express an IL-18 receptor β chain and stimulation by IL-18 enhances the effect of factors such as PI3K/Akt and Bcl2, which augment cell viability (Li Wen et al., J. Leukocyte Biol., 82, 142-151, 2007).

As described above, IL-18 has properties that improve cell viability by inhibiting cell death. Therefore, IL-18 is presumably capable of acting as a cofactor for a bisphosphonate so as to significantly improve the effect of growing Vγ9Vδ2 T cells by a bisphosphonate and IL-2. Thus, the above arrangement allows highly efficient growth of Vγ9Vδ2 T cells.

A method for producing an activated Vγ9Vδ2 T cell of the present invention includes stimulating a Vγ9Vδ2 T cell by at least a bisphosphonate, interleukin 2, and interleukin 18. As described above, the combinational use of a bisphosphonate, IL-2, and IL-18 allows efficient growth of Vγ9Vδ2 T cells. Furthermore, as shown in an example described below, the Vγ9Vδ2 T cells thus proliferated have a high antitumor activity and high cytokine productivity. Thus, the above arrangement allows highly efficient production of Vγ9Vδ2 T cells having superior bioactivities.

An activated Vγ9Vδ2 T cell of the present invention is obtained by stimulation with at least a bisphosphonate, interleukin 2, and interleukin 18.

A Vγ9Vδ2 T cell proliferation kit of the present invention includes at least a Vγ9Vδ2 T cell, a bisphosphonate, interleukin 2, and interleukin 18. According to the above arrangement, materials minimally required for the growth of Vγ9Vδ2

T cells are included as a prepared set. This allows the proliferation of Vγ9Vδ2 T cells to be carried out in a simple and easy manner.

As described above, the Vγ9Vδ2 T cell proliferation agent of the present invention, which includes at least a bisphosphonate, interleukin 2, and interleukin 18, is capable of highly efficiently growing Vγ9Vδ2 T cells, which have conventionally been unable to be proliferated sufficiently. Furthermore, the Vγ9Vδ2 T cell proliferation agent is also capable of providing the Vγ9Vδ2 T cells thus proliferated with a superior antitumor action and superior cytokine productivity.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 2 shows a result of a flow-cytometric analysis on PBMC composition, wherein FIG. 2A shows PBMCs before incubation with zoledronate, IL-2, and IL-18, and FIG. 2B shows PBMCs after incubation with zoledronate, IL-2, and IL-18.

DESCRIPTION OF THE EMBODIMENTS

One embodiment of the present invention will be described below. It should be noted, however, that the present invention is not limited to this embodiment.

(1. Vγ9Vδ2 T Cell Proliferation Agent)

A Vγ9Vδ2 T cell proliferation agent of the present invention contains a bisphosphonate, interleukin 2, and interleukin 18 at least.

Bisphosphonates are a physiologically occurring pyrophosphate analogue, and are two types of bisphosphonates based on what kind of side chains they have: nitrogen-containing bisphosphonates and non-nitrogen-containing bisphosphonates. Based on the kind of derivative attached to the C at the center of the basic skeleton, bisphosphonates are classified into three groups: bisphosphonates with a simple side chain structure, such as etidronate and clodronate; bisphosphonates with an amino group, such as zoledronate, pamidronate, alendronate, resedronate, and ibandronate; and bisphosphonates with a cyclic structure, such as incadronate, risedronate, and minodronate.

The Vγ9Vδ2 T cell proliferation agent according to present invention is not limited to a particular kind of bisphosphonates. Furthermore, the Vγ9Vδ2 T cell proliferation agent according to present invention may contain one or more bisphosphonates. Of bisphosphonates, zoledronate is particularly preferable because of its high ability to stimulate the growth of Vγ9Vδ2 T cells. In addition to its effect of growing Vγ9Vδ2 T cells, zoledronate is known to increase antigenicity of cancer cells against Vγ9Vδ2 T cells by inhibiting farnesyl pyrophosphate synthetase of the cancer cells so that the IPP is expressed on the surface of the cancer cells. Thus, it can be said that zoledronate is particularly preferable.

The bisphosphonate used in the present invention may have any form, and may be a free bisphosphonate, a bisphosphonate salt, or a hydrate of bisphosphonate or bisphosphonate salt, for example. Further, the free bisphosphonate, the salt, and the hydrate may be used solely or in combination. The bisphosphonate salt is not particularly limited, and may be a sodium salt, a potassium salt, or an ammonium salt, for example.

IL-2, known as a T cell proliferator, is used as a cofactor for the bisphosphonate. IL-18 is also used as a cofactor for the bisphosphonate. IL-18 improves cell viability by inhibiting cell death. Thus, it is considered that the addition of IL-18 allows Vγ9Vδ2 T cells to be proliferated more significantly than when only IL-2 acts on the bisphosphonate.

Based on differences in the δ chain, γδ T cells are classified into three subfractions: Vδ1T cells; Vδ2 T cells; and Vδ3T cells. It is Vγ9Vδ2 T cells contained in the Vδ2 T cells that occur in human peripheral blood and are capable of reacting with the bisphosphonate. Therefore, Vγ9Vδ2 T cells are used in the present invention.

The Vγ9Vδ2 T cell proliferation agent of the present invention may be prepared by mixing at least a bisphosphonate, IL-2, and IL-18. The concentration of the bisphosphonate is not particularly limited, and may preferably be in a range from 0.5 μM to 5.0 μM. There is no particular optimal concentration of the IL-2. It is sufficient that the IL-2 be used in a concentration of at least 10 ng/ml or 100 units/ml when the concentration of the bisphosphonate falls within the above range. There is no particular optimal concentration of the IL-18, either. It is sufficient that the IL-18 be used in a concentration of at least 50 ng/ml when the concentration of the bisphosphonate falls within the above range.

In the case where the bisphosphonate, the IL-2, and the IL-18 are added to a culture solution so that their respective final concentrations fall within the above ranges, the concentration of the Vγ9Vδ2 T cells is not particularly limited, and is preferably in a range from about $5 \times 10^3$/ml to $10 \times 10^3$/ml. For example, $5 \times 10^5$/ml to $10 \times 10^5$/ml of peripheral blood mononuclear cells (hereinafter referred to as "PBMC") contain about $5 \times 10^3$/ml to $10 \times 10^3$/ml of Vγ9Vδ2 T cells. The method for the above mixing is not particularly limited. For example, the mixing may be carried out by adding the bisphosphonate, the IL-2, and the IL-18 to water or a conventionally known medium so that their respective concentrations fall within the above ranges, and stirring the mixture by a conventionally known stirrer or the like.

The Vγ9Vδ2 T cell proliferation agent of the present invention may only include a bisphosphonate, IL-2, and IL-18. However, the Vγ9Vδ2 T cell proliferation agent may further contain other components, provided that such other components do not inhibit the bisphosphonate, the IL-2, and the IL-18 from growing Vγ9Vδ2 T cells. For example, the following components may be used if necessary: another cofactor such as IL-15, and additive components such as a medium necessary for the Vγ9Vδ2 T cell incubation, an excipient, a disintegrant, a lubricant, a bonding agent, a preservative, a stabilizer, an emulsifier, an osmoregulating agent, and a base. The Vγ9Vδ2 T cell proliferation agent of the present invention may be prepared so as to include the above additive components by a common preparation technology. The Vγ9Vδ2 T cell proliferation agent may be used in a solid or liquid form such as a tablet, a capsule, powder, a granule, a suppository, cream, ointment, solution, emulsion, an oily formulation, or a suspending agent.

Examples of the additive components include an RPMI 1640 medium containing human type-AB serum, glucose, lactose, starch, carboxymethylcellulose, magnesium stearate, talc, liquid paraffin, polyvinyl alcohol, vegetable oil, glycerine fatty acid ester, polyalkylene glycol, and the like.

Since Vγ9Vδ2 T cells contained in Vδ2 T cells occur in human peripheral blood and have a strong antitumor action, the Vγ9Vδ2 T cells are promising Vδ2 T cells for cancer treatment. However, the absolute number of the Vγ9Vδ2 T cells is extremely small. Therefore, an efficient method for growing the Vγ9Vδ2 T cells is long awaited. The proliferation agent of the present invention is capable of significantly growing the Vγ9Vδ2 T cells by stimulating them when contacted with the Vγ9Vδ2 T cells. In an example described below, the Vγ9Vδ2 T cells were successfully proliferated, although there was variety among individuals, by a factor of about 300 to 3000. In contrast, a conventional proliferation method using zoledronate and IL-2 is merely capable of growing the Vγ9Vδ2 T cells by a factor of up to 800 (see Int. J. Cancer 116, 94-99, 2005).

As described above, it can be said that the proliferation agent of the present invention is highly useful for application of Vγ9Vδ2 T cells to cancer treatment. Furthermore, as described in [2.] below, the Vγ9Vδ2 T cells proliferated using the proliferation agent of the present invention not only have a high proliferated rate, but also can acquire a distinctly strong antitumor action and high cytokine productivity. In this respect also, the proliferation agent of the present invention can be said to be highly useful.

(2. A Method for Producing Activated Vγ9Vδ2 T Cells, the Activated Vγ9Vδ2 T Cells and a Medicine Containing the Same, a Vγ9Vδ2 T Cell Proliferation Kit)

A method for producing activated Vγ9Vδ2 T cells of the present invention includes stimulating Vγ9Vδ2 T cells by at least a bisphosphonate, interleukin 2, and interleukin 18. As a result, activated Vγ9Vδ2 T cells, i.e., Vγ9Vδ2 T cells having a strong antitumor action and high cytokine productivity, can be obtained.

Vγ9Vδ2 T cells to be stimulated may be prepared by a conventionally known method. For example, human peripheral blood or human peripheral blood mononuclear cells are collected, and magnetic beads to which an anti-γδ TCR antibody and/or an anti-Vγ2 T antibody are bonded are allowed to act on the human peripheral blood or the human peripheral blood mononuclear cells, whereby Vγ9Vδ2 T cells can be isolated. However, the isolation is not essential to use Vγ9Vδ2 T cells. For example, it is also possible to isolate activated Vγ9Vδ2 T cells with the above magnetic beads after human blood, human lymph, human peripheral blood mononuclear cells or the like is stimulated by at least a bisphosphonate, interleukin 2, and interleukin 18.

The above stimulation can be carried out by contacting Vγ9Vδ2 T cells with the bisphosphonate, the IL-2, and the IL-18. The contact method is not particularly limited. For example, the above contact can be carried out by adding Vγ9Vδ2 T cells, the bisphosphonate, the IL-2, and the IL-18 to a conventionally known medium (for example, RPMI 1640 medium containing 5% human type-AB serum) suitable for the proliferation of Vγ9Vδ2 T cells, and culturing the Vγ9Vδ2 T cells in a conventionally known incubator such as a $CO_2$ incubator. The incubation temperature and the incubation period are not particularly limited, provided that the Vγ9Vδ2 T cells can be proliferated. The Vγ9Vδ2 T cells are generally incubated at 37° C. in the presence of 5% $CO_2$. The incubation of Vγ9Vδ2 T cells is preferably performed for 10 to 14 days while fresh medium, bisphosphonate, IL-2, and IL-18 are added once every 3 to 5 days.

The bisphosphonate, the IL-2, and the IL-18 may be added to a medium separately. They may also be added in a mixed form as a proliferation agent as explained in [1.], or as a formulated proliferation agent. Further, another cofactor such as IL-15 may be added as well. Contacting Vγ9Vδ2 T cells with the bisphosphonate, the IL-2, and the IL-18 causes the Vγ9Vδ2 T cells to be specifically stimulated so that the Vγ9Vδ2 T cells are proliferated at a distinctly high growth rate, and promotes induction of an antitumor action of the Vγ9Vδ2 T cells and improvement in the cytokine productivity of the Vγ9Vδ2 T cells. This allows producing activated Vγ9Vδ2 T cells, which are Vγ9Vδ2 T cells having a strong antitumor action and high cytokine productivity. The respective concentrations of the bisphosphonate, the IL-2, and the IL-18, and the amount of Vγ9Vδ2 T cells to use are as described above in [1.].

The structural difference between the activated Vγ9Vδ2 T cells of the present invention and Vγ9Vδ2 T cells stimulated by a conventional method is still unknown at present. However, as described in an example below, the activated Vγ9Vδ2 T cells of the present invention are capable of exhibiting a strong antitumor action and cytokine productivity, which is significantly higher than the cytokine productivity of Vγ9Vδ2 T cells stimulated by a conventional method. For example, in the example below, it was confirmed that the activated Vγ9Vδ2 T cells of the present invention exhibited a distinctly high ability to produce IFN-γ, tumor necrosis factor (TNF), and granulocytic macrophage colony stimulating factor (GM-CSF), in comparison with Vγ9Vδ2 T cells stimulated by zoledronate and IL-2.

Because the activated Vγ9Vδ2 T cells have a superior antitumor action and superior cytokine productivity as described above, the present invention further encompasses a medicine containing the activated Vγ9Vδ2 T cells.

The medicine may only include the activated Vγ9Vδ2 T cells, or may include a component such as an additive component described in [1.] other than the activated Vγ9Vδ2 T cells. The medicine is capable of exhibiting its antitumor action and cytokine productivity when the medicine is administered to a human. Applicable administration methods are, for example, local injection, intravenous injection, transdermal absorption, and the like.

Due to its antitumor action and cytokine productivity, the medicine can preferably be used as a medicine for cancer treatment. Cancers for which the medicine of the present invention can be used are not particularly limited. The medicine can be used for various, conventionally known cancers such as mesothelioma, osteosarcoma, kidney cancer, prostate cancer, squamous cancer, lung cancer, melanoma, pancreas cancer, stomach cancer, and liver cancer. In addition, due to its cytokine productivity, the medicine is capable of exhibiting such actions as an antiviral action, an immunoresponse inhibiting action, and an action regulating cell proliferation, cell differentiation and the like. Therefore, the medicine is also capable of being used for diseases of which the above actions are effective for treatment: for example, intractable infectious diseases such as malaria and tuberculosis.

One exemplary usage of the present invention is a Vγ9Vδ2 T cell proliferation kit. To be specifically embodied, the Vγ9Vδ2 T cell proliferation kit is only required to include at least a Vγ9Vδ2 T cell, a bisphosphonate, interleukin 2, and interleukin 18. The proliferation kit may be accompanied by a medium for culturing the Vγ9Vδ2 T cells, and/or an experimental material such as a culture plate according to need.

The proliferation kit of the present invention may be provided in such a manner that the Vγ9Vδ2 T cells, the bisphosphonate, the interleukin 2, the interleukin 18, and the other reagent are all provided in a single container in their respective appropriate volumes and/or forms, or are provided individually in separate containers. In addition, the kit of the present invention may also include a manual for showing, for example, a procedure for implementing the above method of the present invention.

The present invention can be described as follows.

In the Vγ9Vδ2 T cell proliferation agent of the present invention, the bisphosphonate may preferably be zoledronate. Among other bisphosphonates, the compound zoledronate has a high ability to stimulate the proliferation of Vγ9Vδ2 T cells. This allows the above arrangement to implement efficient proliferation of Vγ9Vδ2 T cells.

The medicine of the present invention includes the activated Vγ9Vδ2 T cells of the present invention.

As shown in an example described below, the activated Vγ9Vδ2 T cells have cytokine productivity superior to the cytokine productivity of conventional Vγ9Vδ2 T cells, and have a high antitumor activity. Therefore, the medicine including the activated Vγ9Vδ2 T cells is capable of exhibiting, for example, a superior anticancer action, antiviral action, immunoresponse inhibiting action, action regulating cell proliferation, cell differentiation or the like.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

Example 1

Proliferation of Vγ9Vδ2 T Cells

Peripheral blood was collected from a healthy adult, and PBMCs were separated from the peripheral blood by Ficoll-Hypaque density gradient centrifugation (conditions: at 2000 rpm for 20 minutes at room temperature (25° C.), using a swing rotor TS-7 (available from TOMY SEIKO Co., Ltd.)).

A PRMI 1640 medium containing 5% human type-AB serum was supplemented with zoledronate (with a final concentration of 1 µM), IL-2 (with a final concentration of 10 ng/ml), and IL-18 (with a final concentration of 100 ng/ml). The PBMCs were suspended in the culture solution so as to occur in a concentration of $5\times10^5$/ml to $10\times10^5$/ml. As shown in (e) of FIG. 2, the PBMCs contained about 1% to 5% Vγ9Vδ2 T cells.

The PBMCs were cultured in a $CO_2$ incubator at 37° C. in the presence of 5% $CO_2$ for 14 days during which a fresh medium was added therein every 3 to 5 days. The fresh medium was prepared by adding zoledronate, IL-2, and IL-18 to the fresh medium so as to reach the above respective concentrations, the fresh medium having an amount three to five times more than the medium used at the initiation of the incubation. The addition of fresh medium aimed at preventing hyperproliferation of the cells (i.e., to prevent the culture solution from turning yellow). The zoledronate, the IL-2, and the IL-18 used in the proliferation were obtained from Novartis Pharma K.K., R&D Systems Inc., and GlaxoSmithKline K.K., respectively.

The proliferated Vγ9Vδ2 T cells were analyzed by flow cytometry with use of a marker antibody against an antigen expressed on the surface of the cells (used apparatus: FACS-Calibur, BECTON DICKINSON Co., Ltd.). The absolute number of the Vγ9Vδ2 T cells was calculated from (i) the ratio of the Vγ9Vδ2 T cells to the entire cells and (ii) the absolute number of the entire cells.

A similar experiment was conducted using zoledronate (1 µM) and IL-2 (10 ng/ml) as a control.

For the purpose of determining the role played by IL-18 in the proliferation of Vγ9Vδ2 T cells, an anti-IL-18 receptor antibody (available from R&D Systems Inc.) of 2.5 µg/ml was added in to a medium supplemented with zoledronate (1 µM) and IL-2 (10 ng/ml), so as to block endogenous IL-18.

Figure 1A:
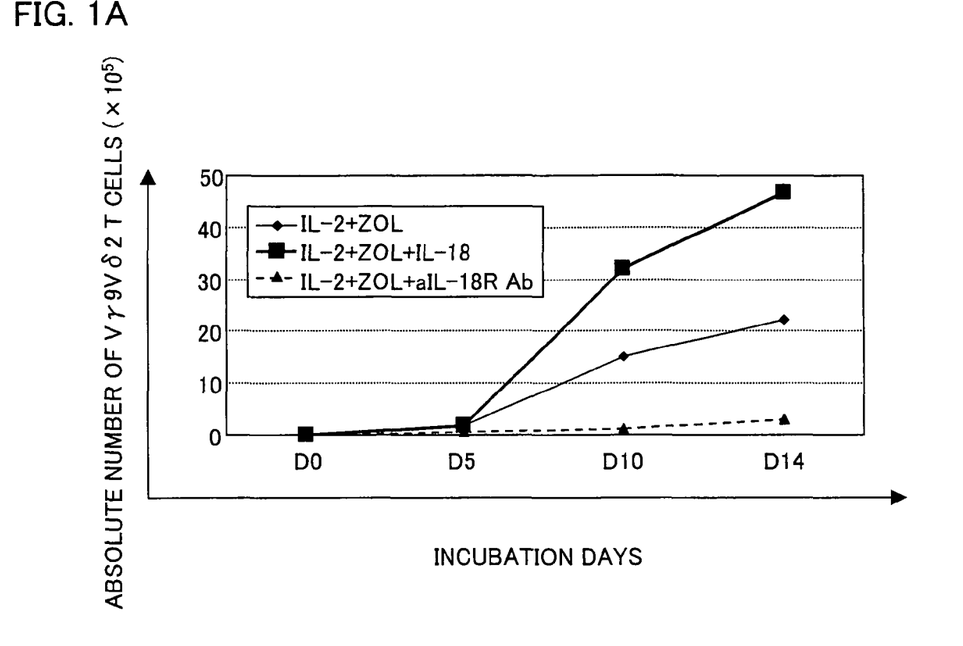
FIG. 1A is a graph illustrating a result of proliferation of Vγ9Vδ2 T cells from peripheral blood of a 62-year-old male, the graph demonstrating an effect of exogenous IL-18 on the proliferation of the Vγ9Vδ2 T cells stimulated by zoledronate in the presence of IL-2.
Figure 1B:
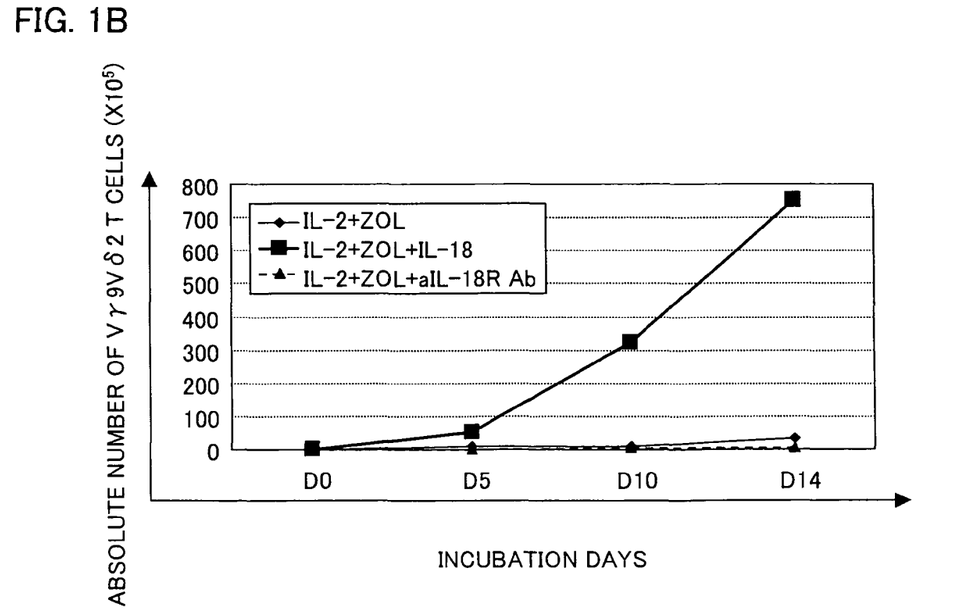
FIG. 1B is a graph illustrating a result of proliferation of Vγ9Vδ2 T cells from peripheral blood of a 31-year-old female, the graph demonstrating the effect of exogenous IL-18 on the proliferation of the Vγ9Vδ2 T cells stimulated by zoledronate in the presence of IL-2.
Figure 2:
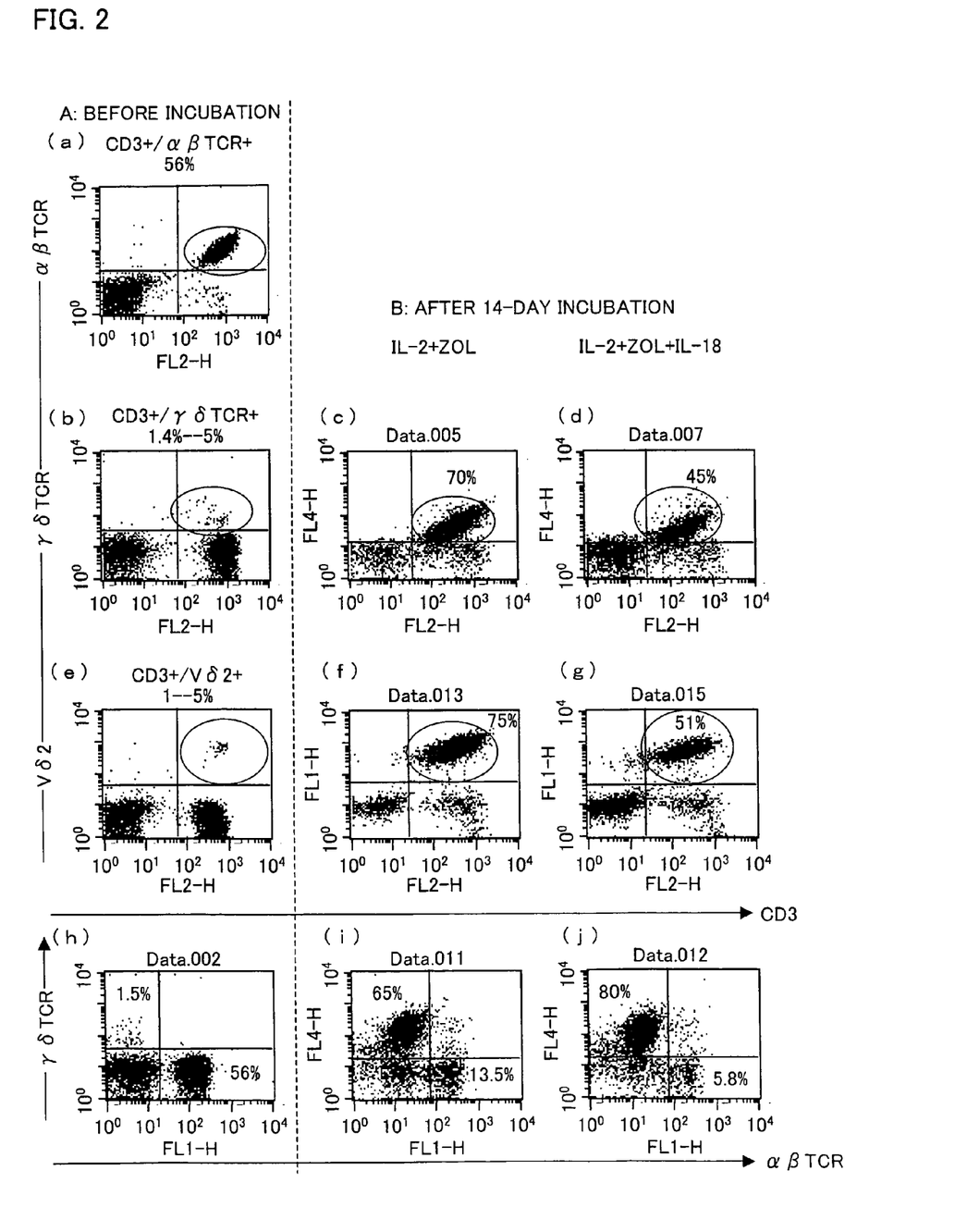

The result is shown in FIGS. 1A, 1B and 2. FIGS. 1A and 1B each demonstrate the effect of exogenous IL-18 on the proliferation of Vγ9Vδ2 T cells stimulated by the zoledronate in the presence of the IL-2. FIG. 1A shows the result of the proliferation of Vγ9Vδ2 T cells from peripheral blood of a 62-year-old man. FIG. 1B shows the result of the proliferation of Vγ9Vδ2 T cells from peripheral blood of a 31-year-old woman. In FIGS. 1A and 1B, "ZOL" and "aIL-18R Ab" refer to zoledronate and an anti-IL-18 receptor antibody, respectively, and the vertical axis represents the absolute number of Vγ9Vδ2 T cells.

When PBMCs separated from the human peripheral blood were cultured in a culture solution supplemented with zoledronate, IL-2, and IL-18, the total number of the PBMCs (not shown) increased, although there was variety among individuals, by a factor of about 40 to 100. In particular, the number of Vγ9Vδ2 T cells increased significantly (see FIGS. 1A, 1B and 2). In contrast, when the PBMCs were cultured in a culture solution supplemented with only zoledronate and IL-2, the total number of the PBMCs increased merely by a factor of about 10 (not shown).

In the experimental system of FIG. 1A, the number of Vγ9Vδ2 T cells at the initiation (D0) of the incubation was about $2.5\times10^3$, and the Vγ9Vδ2 T cells were proliferated to about $48\times10^5$ after the 14-day incubation (D14). In the experimental system of FIG. 1B, the number of Vγ9Vδ2 T cells at the initiation (D0) of the incubation was about $6\times10^3$, and the Vγ9Vδ2 T cells were proliferated to about $750\times10^5$ after the 14-day incubation (D14).

As described above, it was confirmed that, when the Vγ9Vδ2 T cells were cultured in the culture solution supplemented with the zoledronate, the IL-2, and the IL-18, the number of the Vγ9Vδ2 T cells increased by a factor of at least about 300 to 3000. Thus, it was proven that the growth rate was, although varying depending on subjects, significantly high when the zoledronate, the IL-2, and the IL-18 were added to the culture solution, as compared to when only the zoledronate and the IL-2 were added.

In addition, as indicated by the dotted lines in the graphs of FIGS. 1A and 1B, the addition of the anti-IL-18 receptor antibody inhibited the IL-18 from acting on the Vγ9Vδ2 T cells, whereby almost no proliferation of the Vγ9Vδ2 T cells was observed. This also proves that the IL-18 played a critical role in the proliferation of Vγ9Vδ2 T cells.

An increase in the number of Vγ9Vδ2 T cells was not observed in the culture solution supplemented with only the IL-18 and the zoledronate. This demonstrates that the IL-2 is essential for the proliferation of Vγ9Vδ2 T cells. A significant increase in the number of Vγ9Vδ2 T cells was observed in the culture solution supplemented with only the IL-2 and the IL-18. However, the increase was much smaller than when Vγ9Vδ2 T cells were cultured in the culture solution supplemented with the zoledronate, the IL-2, and the IL-18. These results show that it is useful to add not only the IL-2 and the zoledronate as conventionally added, but also the IL-18 to a culture solution, for the purpose of obtaining Vγ9Vδ2 T cells in a number sufficient for therapeutic use.

FIG. 2 shows the result of a flow-cytometric analysis of the PBMC composition. In FIG. 2, (a), (b), (e), and (h) to the left of the dotted line each show the PBMCs before the incubation with the zoledronate, the IL-2, and the IL-18 (hereinafter referred to simply as "before the incubation"), whereas each graph to the right of the dotted line shows the PBMCs after the incubation with the zoledronate, the IL-2, and the IL-18.

FIG. 2(a) shows that 56% of the PBMCs before the incubation were αβ T cells. The cells within the circle in FIG. 2(a) are αβ T cells. FIG. 2(b) shows that 1.4% to 5% of the PBMCs before the incubation were Vγ9Vδ2 T cells. FIG. 2(c) shows that, after the PBMCs were cultured for 14 days with the zoledronate and the IL-2, Vγ9Vδ2 T cells increased to 70% of the entire PBMCs. FIG. 2(d) shows that, after the PBMCs were cultured for 14 days with the zoledronate, the IL-2, and the IL-18, Vγ9Vδ2 T cells increased to 45% of the entire PBMCs.

As described above, when the PBMCs separated from the human peripheral blood were cultured in the culture solution supplemented with the zoledronate, the IL-2, and the IL-18, the total number of the PBMCs increased from the number of the PBMCs before the incubation by a factor of about 40 to 100. Meanwhile, when the PBMCs were cultured in the culture solution supplemented with only the zoledronate and the IL-2, the total number of the PBMCs increased from the number of the PBMCs before the incubation merely by a factor of about 10. Thus, between FIG. 2(c) and FIG. 2(d), the total number of the PBMCs is far larger in FIG. 2(d). This shows that 45% of the PBMCs in FIG. 2(d) greatly outnumber 70% of the PBMCs in (c) of FIG. 2. This proves that Vγ9Vδ2 T cells can be proliferated far more efficiently when the zoledronate, the IL-2, and the IL-18 were used, than when only the zoledronate and the IL-2 were used.

FIG. 2(e) shows that 1% to 5% of the PBMCs before the incubation were Vγ9Vδ2 T cells. FIG. 2(f) shows that, after the PBMCs were cultured for 14 days with the zoledronate and the IL-2, Vγ9Vδ2 T cells increased to 75% of the entire PBMCs. FIG. 2(g) shows that, after the PBMCs were cultured for 14 days with the zoledronate, the IL-2, and the IL-18, Vγ9Vδ2 T cells increased to 51% of the entire PBMCs.

FIG. 2(h) shows that 56% of the PBMCs before the incubation were αβ T cells, and that 1.5% of the PBMCs before the incubation were Vγ9Vδ2 T cells. FIG. 2(i) shows that, after the PBMCs were cultured for 14 days with the zoledronate and the IL-2, Vγ9Vδ2 T cells increased to 65% of the entire PBMCs, and that the αβ T cells had decreased to 13.5% of the entire PBMCs. FIG. 2(j) shows that, after the PBMCs were cultured for 14 days with the zoledronate, the IL-2, and the IL-18, Vγ9Vδ2 T cells increased 80% of the entire PBMCs were, and that the αβ T cells decreased to 5.8% of the entire PBMCs.

As described above, it was proven that, when PBMCs are cultured with the zoledronate, IL-2, and IL-18, Vγ9Vδ2 T cells can be proliferated highly efficiently compared to when PBMCs are cultured with zoledronate and IL-2.

Example 2

Physiological Action of Activated Vγ9Vδ2 T Cells

Example 2-1

Expression of Surface Antigen NKG2D

Figure 3A:
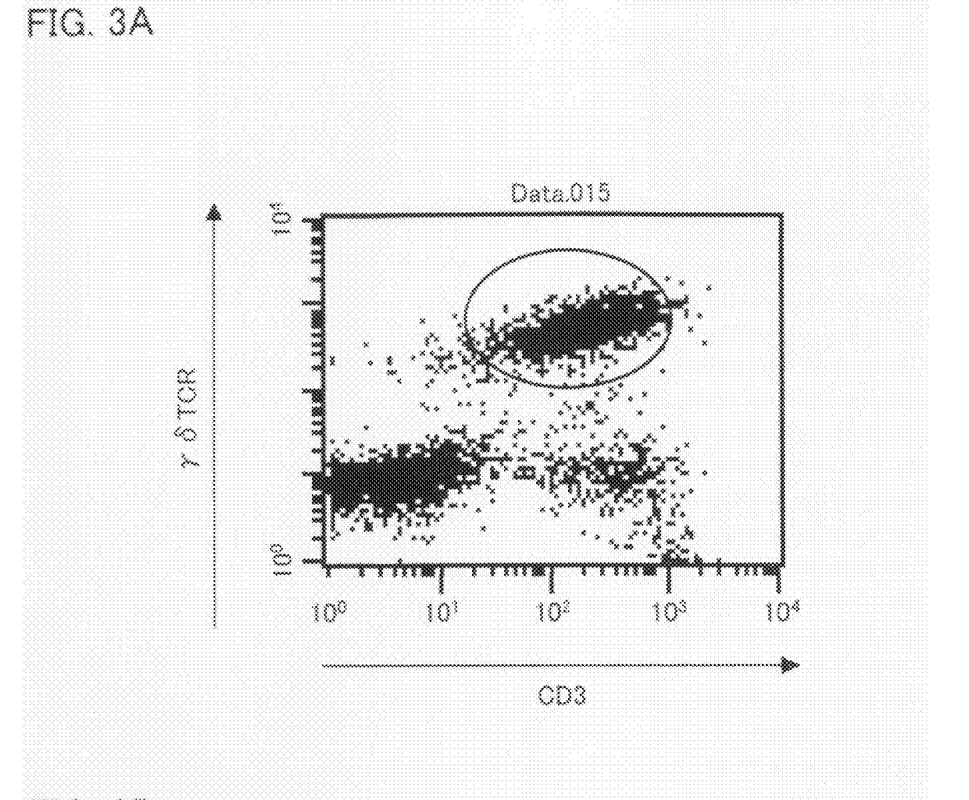
FIG. 3A is a view illustrating that 14-day incubation with zoledronate, IL-2, and IL-18 increased Vγ9Vδ2 T cells to account for 51% of entire PBMCs.
Figure 3B:
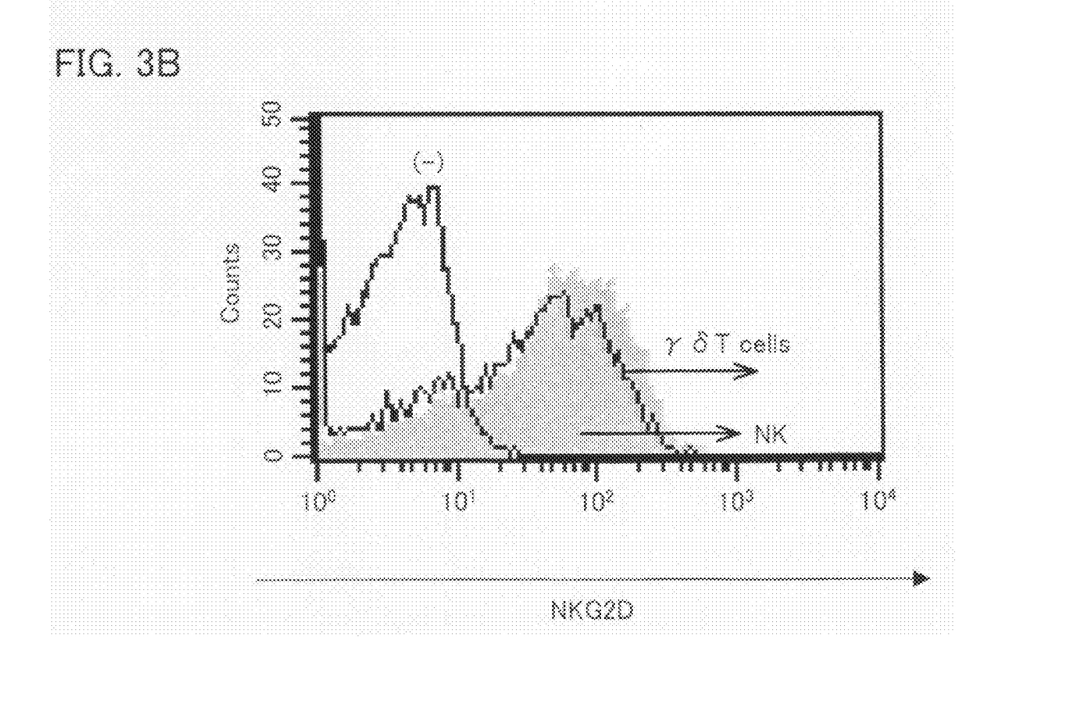
FIG. 3B is a view illustrating that NKG2D was strongly expressed in Vγ9Vδ2 T cells stimulated by IL-2, zoledronate, and IL-18.

Flow-cytometric analysis of the Vγ9Vδ2 T cells (activated Vγ9Vδ2 T cells) proliferated through stimulation by the IL-2, the zoledronate, and the IL-18 as described above was conducted. The flow-cytometric analysis showed that the Vγ9Vδ2 T cells strongly expressed NKG2D, which plays a critical role in antitumor action. This suggests that the activated Vγ9Vδ2 T cells had a strong antitumor action. FIG. 3A shows the expression of NKG2D on the activated Vγ9Vδ2 T cells. FIG. 3A is identical to FIG. 2(g). The cells within the circle are Vγ9Vδ2 T cells. It is clear from FIG. 3B that the Vδ2 T cells stimulated by the IL-2, the zoledronate, and the IL-18 strongly expressed NKG2D.

Example 2-2

Cytocidal Activity Against Tumor Cells

The cytocidal activity of the Vγ9Vδ2 T cells against tumor cells was evaluated by performing BLT analysis of serine esterase released as a result of overnight coincubation of various tumor cells (target) and the Vγ9Vδ2 T cells (effecter) in various ratios, and calculating the ratio of lysed target tumor cells to the original tumor cells. The cytocidal activity of the Vγ9Vδ2 T cells against tumor cells was assayed with respect to each of (i) three kinds (MESO-1, MESO-4, MSTO-211H) of tumor cells established from a mesothelioma, (ii) a normal mesothelial cell Met5A, and (iii) a cell established from an osteosarcoma, in the effecter-to-target ratios of 1:1, 3:1, and 10:1.

Figure 4A:
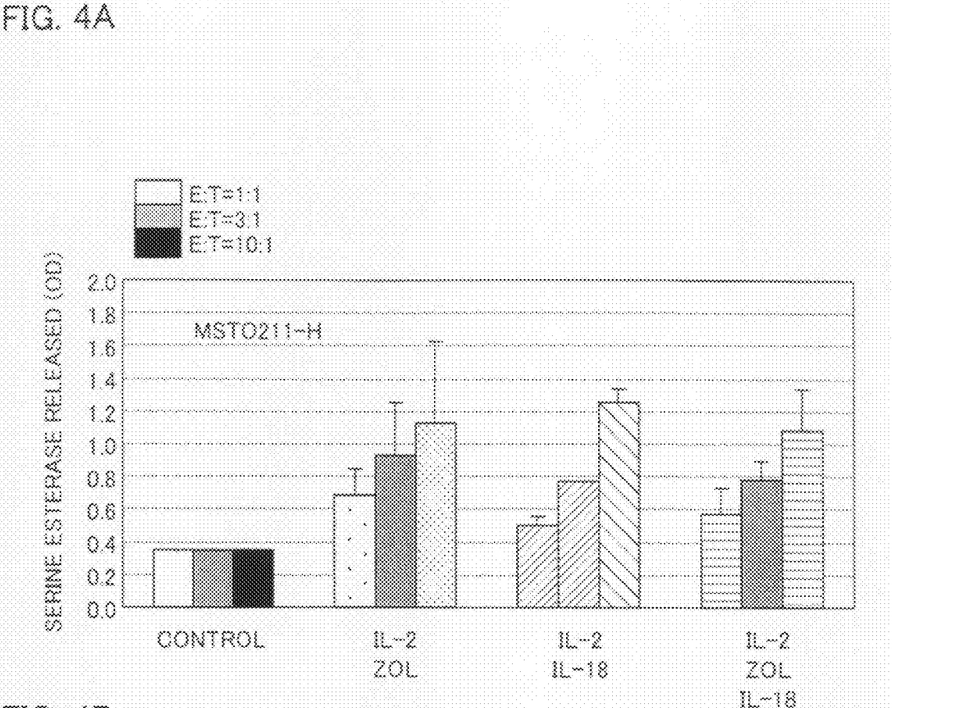
FIG. 4A is a graph illustrating a cytocidal activity of Vγ9Vδ2 T cells against MSTO-211H.
Figure 4B:
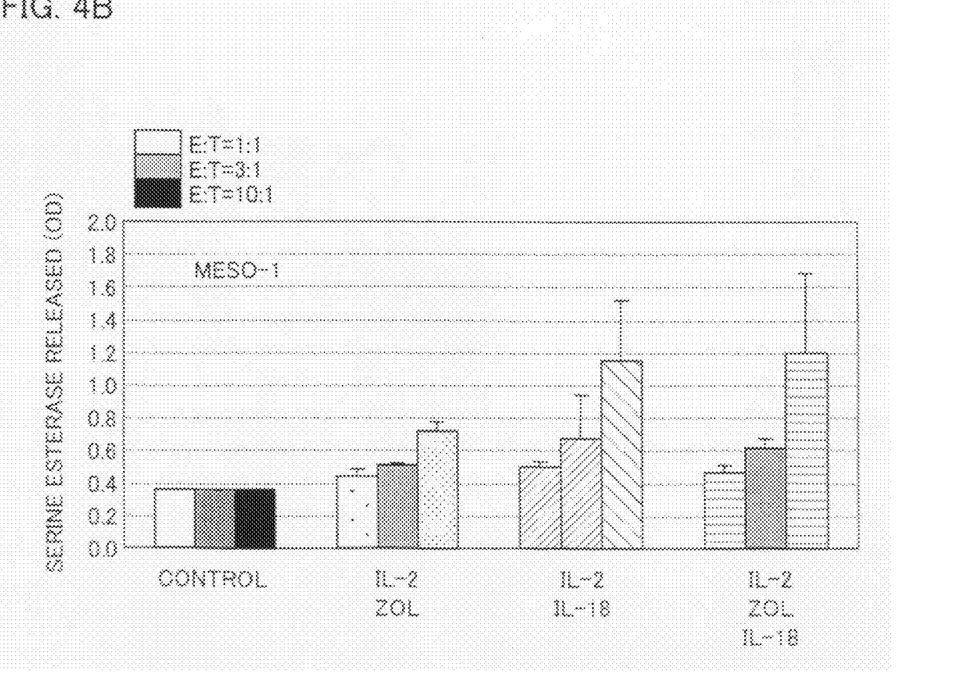
FIG. 4B is a graph illustrating a cytocidal activity of the Vγ9Vδ2 T cells against MESO-1.

FIGS. 4A and 4B are each a graph illustrating a cytocidal activity of the Vγ9Vδ2 T cells, targeted to MSTO-211H and MESO-1, respectively. In each of FIGS. 4A and 4B, the horizontal axis represents the effecter; "CONTROL" represents unstimulated Vγ9Vδ2 T cells; "IL2 ZOL" represents Vγ9Vδ2 T cells stimulated by the IL-2 and the zoledronate; "IL2 IL-18" represents Vγ9Vδ2 T cells stimulated by the IL-2 and the IL-18; and "IL2 ZOL IL-18" represents Vγ9Vδ2 T cells stimulated by the IL-2, the zoledronate, and IL-18. The legend to each of FIGS. 4A and 4B shows that the white bar, the gray bar, and the black bar correspond to the effecter-to-target (E-to-T) ratios of 1:1, 3:1, and 10:1, respectively. Although only the bars in the "CONTROL" conform to the legend, the three bars in each of the other experimental plots correspond to the E-to-T ratios of 1:1, 3:1, and 10:1, respectively from the left, as in the "CONTROL".

A high cytocidal activity against tumor cells was exhibited by each of (i) the Vγ9Vδ2 T cells cultured in the culture solution supplemented with the zoledronate, the IL-2, and the IL-18, and (ii) the Vγ9Vδ2 T cells cultured in the culture solution supplemented with only the zoledronate and the IL-2. There was no noticeable difference between the respective cytocidal activities. Each of the effecters scarcely exhibited a cytocidal activity (not shown) against Met5A, i.e., a normal mesothelial cell used as a control.

Example 2-3

Production of IFN-γ, TNF, and GM-CSF

Figure 5A:
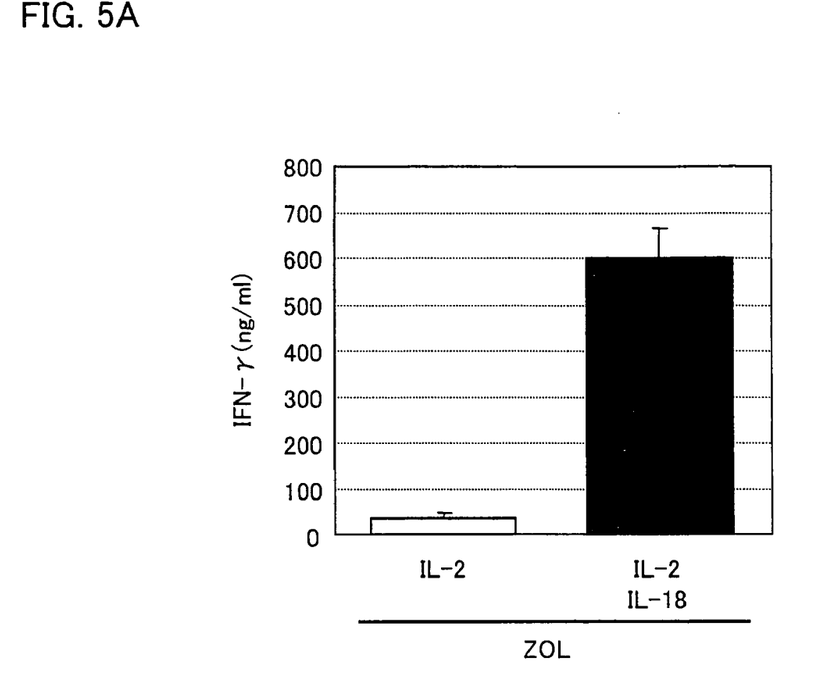
FIG. 5A is a graph illustrating IFN-γ production by Vγ9Vδ2 T cells cultured with zoledronate, IL-2, and IL-18 for one week.
Figure 5B:
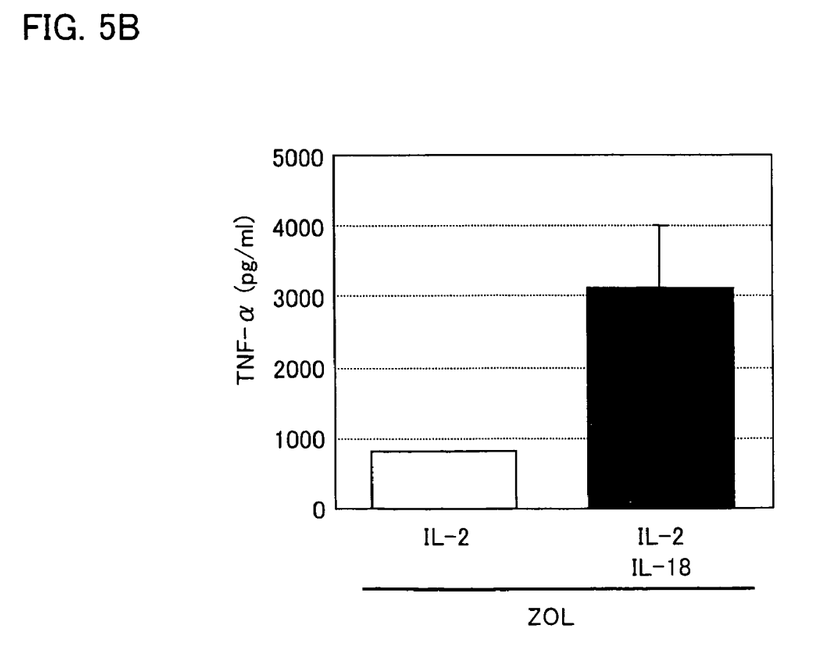
FIG. 5B is a graph illustrating TNFα production by Vγ9Vδ2 T cells cultured with zoledronate, IL-2, and IL-18 for one week.

Supernatants of the culture solutions having various conditions under which Vγ9Vδ2 T cells were cultured were assayed by ELISA so that the production of cytokines (e.g., IFN-γ, TNF, GM-CSF) was measured. FIGS. 5A and 5B are graphs illustrating the IFN-γ production and the TNFα production, respectively, by Vγ9Vδ2 T cells which had been cultured with the zoledronate, the IL-2, and the IL-18 for one week.

As shown in FIGS. 5A and 5B, regarding the amount of cytokines one week after the initiation of the incubation, a supernatant of the culture solution in which Vγ9Vδ2 T cells (activated Vγ9Vδ2 T cells) were cultured with the zoledronate, the IL-2, and the IL-18 contained about 100 times as much IFN-γ and about four times as much tumor necrosis factor (TNF) as a supernatant of the culture solution in which Vγ9Vδ2 T cells were cultured with only the zoledronate and the IL-2.

The Vγ9Vδ2 T cells (activated Vγ9Vδ2 T cells) proliferated as a result of the two-week incubation with the zoledronate, the IL-2, and the IL-18, were purified with use of magnetic beads to which an anti-γδ TCR antibody was bonded, so as to have a purity of 95% or more. The Vγ9Vδ2 T cells were restimulated both in the presence of IL-18 and in the absence of IL-18. After 24 hours, a supernatant of the culture solution containing IL-18 and a supernatant of the culture solution devoid of IL-18 were compared. In this case also, the result obtained was similar to the above. Specifically, the supernatant of the culture solution in which the Vγ9Vδ2 T cells were cultured in the presence of IL-18 had a far larger production of IFN-γ and TNFα.

Furthermore, the production of GM-CSF contained in the supernatant of the culture solution supplemented with IL-18 was also about 10 times as large (data not shown). As described above, IL-18 is capable of not only promoting the proliferation of Vγ9Vδ2 T cells, but also significantly increasing the productivity of IFN-γ and TNF. Therefore, IL-18 is considered to have an action which targets Vγ9Vδ2 T cells toward cancer cells.

Example 2-4

In-vivo Antitumor Effect

Figure 6:
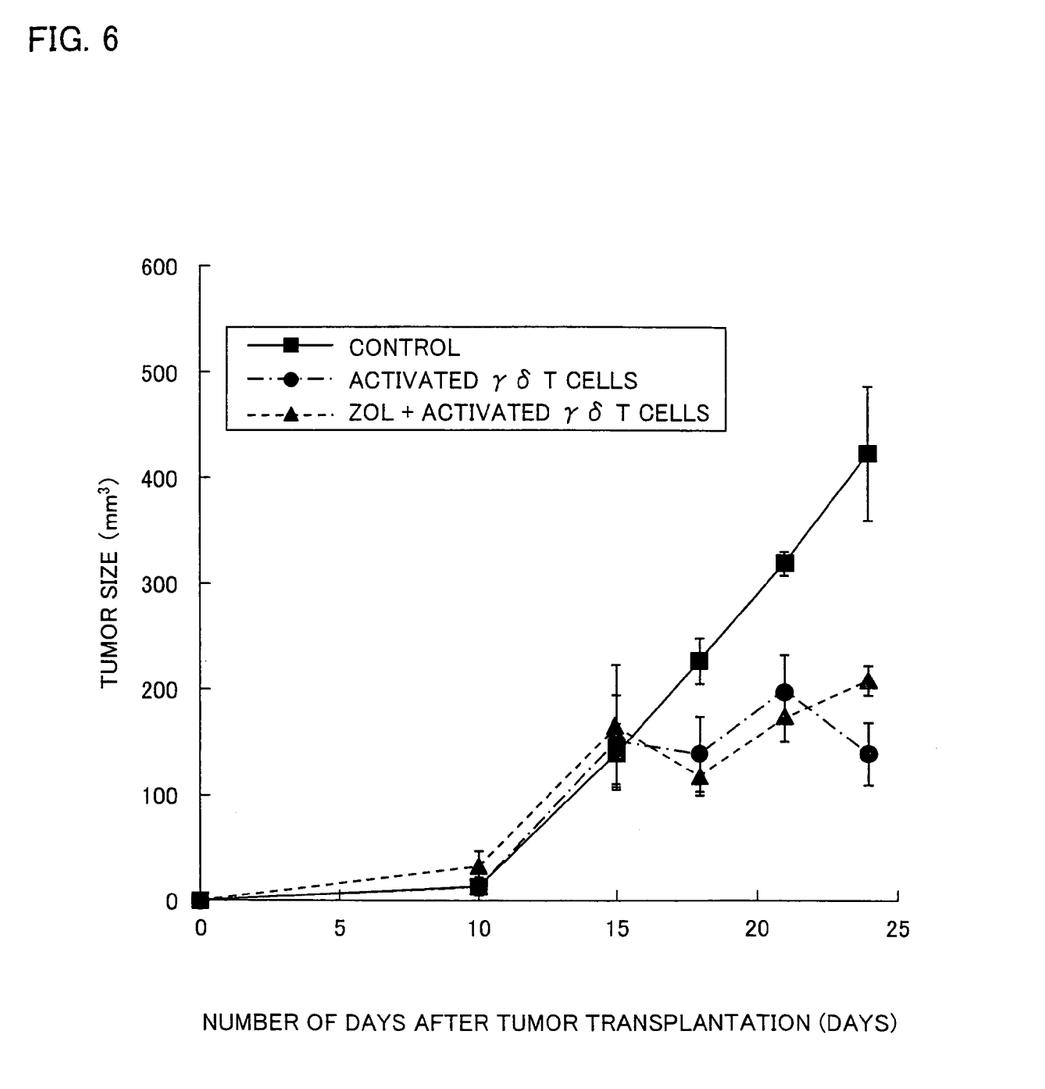
FIG. 6 is a graph illustrating a result of assay of the in-vivo antitumor effect of activated Vγ9Vδ2 T cells.

The in-vivo antitumor effect of the Vγ9Vδ2 T cells was evaluated by transplanting $2\times10^6$ tumor cells derived from a human mesothelioma subcutaneously into a NOD scid mouse, injecting $10^7$ Vγ9Vδ2 T cells once every one week or so into a tail vein of the mouse after the tumor reached about 0.5 cm in diameter, and monitoring the size of the tumor at appropriate intervals. The size (volume) of the tumor was calculated using the following expression: (major axis of the tumor)×(minor axis of the tumor)$^2$×π÷6. FIG. 6 is a graph illustrating the result of assay of the in-vivo antitumor effect of the activated Vγ9Vδ2 T cells.

The Vγ9Vδ2 T cells used were Vγ9Vδ2 T cells (activated Vγ9Vδ2 T cells) stimulated by zoledronate (1 μM), IL-2 (10 ng/ml), and IL-18 (100 ng/ml), in the manner described in Example 1. In FIG. 6, the black dots show the result with regard to the above tumor cells and the activated Vγ9Vδ2 T cells. The result is shown as "ACTIVATED γδ T CELLS" in the legend.

Zoledronate is capable of increasing susceptibility of cancer cells to Vγ9Vδ2 T cells by inhibiting the action of farnesyl pyrophosphate synthase so that isopentenyl pyrophosphate (IPP) and the like are cytoplasmically accumulated in the cancer cells. In view of this, 0.2 ml of zoledronate solution of 1 mM zoledronate content (prepared by dissolving zoledronate in physiological saline) was intraperitoneally administered to a NOD scid mouse in advance, and, after 6 to 16 hours, $10^7$ activated Vγ9Vδ2 T cells were injected into a tail vein of the mouse. In FIG. 6, the black triangles show the result with regard to the tumor cells thus obtained. The result is shown as "ZOL+ACTIVATED γδ T CELLS" in the legend.

A control used here was tumor cells prepared by injecting 0.2 ml of physiological saline, instead of the zoledronate, the IL-2 and the Vγ9Vδ2 T cells, into a NOD scid mouse either from an abdominal cavity or a tail vein.

As shown in FIG. 6, the administration of the Vγ9Vδ2 T cells (activated Vγ9Vδ2 T cells) cultured in the culture solution supplemented with the zoledronate, the IL-2, and the IL-18, caused the size of the tumor 25 days after the transplantation of the tumor to be about a half of that of the control group. This demonstrates that increase in the tumor cells was strongly inhibited. Further, this shows that the Vγ9Vδ2 T cells (activated Vγ9Vδ2 T cells) proliferated efficiently with the use of IL-18 maintained their high antitumor activity even in vivo, and that the Vγ9Vδ2 T cells may be used for treatment of a mesothelioma and the like.

The above observation proved that it is possible to highly efficiently proliferate Vγ9Vδ2 T cells by stimulating such cells by a bisphosphonate, IL-2, and IL-18. Furthermore, the Vγ9Vδ2 T cells thus obtained (activated Vγ9Vδ2 T cells) have a high ability to produce cytokines such as IFN-γ, tumor necrosis factor (TNF), and GM-CSF, and maintain a high cytocidal activity against various tumor cells both in vitro (in a test tube) and in vivo (in a living body). As described above, the use of IL-18 besides a bisphosphonate and IL-2 allows producing, from lymphocytes of the patient's own, as many Vγ9Vδ2 T cells as necessary for use in cancer treatment more readily than conventional methods.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A Vγ9Vδ2 T cell proliferation agent comprising at least zoledronate, interleukin 2, and interleukin 18.

2. A method for producing an activated Vγ9Vδ2 T cell, comprising:
   stimulating a Vγ9Vδ2 T cell with at least zoledronate interleukin 2, and interleukin 18.

3. A Vγ9Vδ2 T cell proliferation kit comprising at least a Vγ9Vδ2 T cell, zoledronate, interleukin 2, and interleukin 18.

* * * * *